(12) United States Patent
Ulrich et al.

(10) Patent No.: US 6,806,256 B2
(45) Date of Patent: Oct. 19, 2004

(54) TASTE MASKED LIQUID PHARMACEUTICAL COMPOSITIONS

(75) Inventors: Stephen A. Ulrich, Cherry Hill, NJ (US); Karen R. Zimm, Stockton, NJ (US); Marc Karel Jozef Francois, Kapellen (BE); Willy Maria Albert Carlo Dries, Merksplas (BE)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/083,776

(22) Filed: Feb. 26, 2002

(65) Prior Publication Data

US 2003/0032600 A1 Feb. 13, 2003

Related U.S. Application Data

(60) Provisional application No. 60/273,472, filed on Mar. 5, 2001.

(51) Int. Cl.⁷ ............... A61K 38/05; A61K 31/497; A61K 31/4709; A61K 31/496
(52) U.S. Cl. ............... 514/19; 514/192; 514/300; 514/253.8
(58) Field of Search ............... 424/494, 497, 424/184.1; 514/19, 192, 253.8, 29, 300, 312, 253.04

(56) References Cited

U.S. PATENT DOCUMENTS

| | | | |
|---|---|---|---|
| 3,485,719 A | 12/1969 | Rogovin | |
| 4,752,580 A | 6/1988 | Downs | |
| 4,780,309 A | 10/1988 | Geria et al. | |
| 4,931,293 A | 6/1990 | Cherukuri et al. | |
| 4,945,087 A | 7/1990 | Talwar et al. | |
| 4,981,698 A | 1/1991 | Cherukuri et al. | |
| 5,004,595 A | 4/1991 | Cherukuri et al. | |
| 5,013,557 A | 5/1991 | Tai | |
| 5,013,716 A | 5/1991 | Cherukuri et al. | |
| 5,057,328 A | 10/1991 | Cherukuri et al. | |
| 5,077,053 A | 12/1991 | Kuncewitch et al. | |
| 5,272,137 A | 12/1993 | Blase et al. | |
| 5,288,498 A | 2/1994 | Stanley et al. | |
| 5,298,238 A | 3/1994 | Hussein et al. | |
| 5,374,659 A | 12/1994 | Gowan, Jr. | |
| 5,409,907 A | 4/1995 | Blasé et al. | |
| 5,520,942 A | 5/1996 | Sauer, Jr. et al. | |
| 5,534,552 A | 7/1996 | Bapat | |
| 5,587,172 A | 12/1996 | Cherukuri et al. | |
| 5,621,005 A | 4/1997 | Gowan, Jr. | |
| 5,658,919 A | 8/1997 | Ratnaraj et al. | |
| 5,674,522 A | 10/1997 | Shah et al. | |
| 5,707,975 A | 1/1998 | Francois et al. | |
| 5,730,997 A * | 3/1998 | Lienhop et al. ............. | 424/439 |
| 5,811,079 A | 9/1998 | Yu et al. | |
| 5,846,557 A | 12/1998 | Eisenstadt et al. | |
| 5,855,908 A | 1/1999 | Stanley et al. | |
| 5,869,098 A | 2/1999 | Misra et al. | |
| 5,876,759 A | 3/1999 | Gowan, Jr. | |
| 5,895,664 A | 4/1999 | Cherukuri et al. | |
| 5,942,211 A | 8/1999 | Harper et al. | |
| 5,998,436 A | 12/1999 | Yazaki et al. | |
| 6,001,392 A | 12/1999 | Wen et al. | |
| 6,090,401 A | 7/2000 | Gowan, Jr. et al. | |
| 6,143,786 A | 11/2000 | Gohman et al. | |
| 6,156,903 A | 12/2000 | Yazaki et al. | |
| 6,165,112 A | 12/2000 | Morris | |
| 6,180,621 B1 | 1/2001 | Kawamoto et al. | |
| 6,184,230 B1 | 2/2001 | Watanabe et al. | |
| 6,239,141 B1 * | 5/2001 | Allen et al. ............. | 514/300 |
| 6,391,886 B1 * | 5/2002 | Lee ............. | 514/289 |
| 6,482,823 B1 * | 11/2002 | Yu et al. ............. | 514/228.8 |

FOREIGN PATENT DOCUMENTS

| | | |
|---|---|---|
| EP | 0620001 A1 | 10/1994 |
| EP | 0 855 183 A2 | 7/1998 |
| EP | 1188441 A1 | 3/2002 |
| EP | 1190720 A1 | 3/2002 |
| GB | 810537 A | 3/1959 |
| WO | WO 97/27750 A1 | 8/1997 |
| WO | WO 00/06122 | 2/2000 |
| WO | WO 00/54811 | 9/2000 |
| WO | WO 00/74685 A1 | 12/2000 |
| WO | WO 00/76549 A1 | 12/2000 |
| WO | WO 01/03698 A1 | 1/2001 |

OTHER PUBLICATIONS

Vanden Bussche, Heather L. et al., "Stability of levofloxacin in an extemporaneously compounded oral liquid", Am J Health–Syst Pharm; vol. 56; Nov. 15, 1999; pp 2316–2318.

* cited by examiner

*Primary Examiner*—Blessing M. Fubara

(57) ABSTRACT

This invention is directed to a taste masked liquid pharmaceutical composition comprising a pharmaceutically active agent and a taste masking composition. In particular, the taste masking composition comprises a taste masking effective amount of an artificial sweetener.

8 Claims, No Drawings

TASTE MASKED LIQUID PHARMACEUTICAL COMPOSITIONS

CROSS REFERENCE TO RELATED APPLICATIONS

This application claims benefit of provisional application Serial No. 60/273,472, filed 5 Mar. 2001, which is hereby incorporated by reference.

FIELD OF THE INVENTION

The present invention relates to novel taste masked liquid pharmaceutical compositions for oral administration. In particular, this invention relates to taste masked liquid pharmaceutical compositions comprising a pharmaceutically active agent and a taste masking composition. More particularly, the taste masking composition comprises a taste masking effective amount of an artificial sweetener.

BACKGROUND OF THE INVENTION

Orally administered drugs are provided to the patient in many dosage forms, including solid forms such as capsules, caplets or tablets and liquid forms such as solutions, syrups, emulsions or suspensions. Pharmaceutically active agents administered in solid dosage form are usually intended to be swallowed whole. The disagreeable taste of the drug is generally not of concern when formulating oral solid dosage forms, because the pharmaceutical's taste can be easily masked with an exterior coating.

Children, older persons, and many other persons including disabled or incapacitated patients often have trouble swallowing tablets or capsules. In these situations, it is desirable to provide the drug either in a chewable solid form or a liquid form. For many patients, including pediatric and geriatric patients, a liquid oral dosage form is preferred over a chewable dosage form. A liquid dosage is especially preferred for this class of patients because of the ease with which it may be swallowed. Additionally, patients may be more inclined to comply with their medication instruction if the dosages are easier to ingest.

Many liquid pharmaceutical compositions formulated for use by pediatric or geriatric patients are often prepared by grinding a tablet dosage form into a powder and mixing the powder with a diluent. Such a formulation often allows much of the drug to remain undissolved, thereby affecting the therapeutic concentration of drug in the composition. In addition, the powder exposes the unpleasant tasting pharmaceutically active agent, thus further requiring a means of masking the taste. It is readily understood that such compositions are impractical and may result in underdosing or overdosing a patient.

A common formulation problem associated with liquid pharmaceutical dosage forms (such as solutions (including syrups) or suspensions) is masking the disagreeable taste that a pharmaceutically active agent may often manifest when administered in a liquid dosage form. Many active ingredients, such as antibiotics, possess a strong, unpleasant and bitter taste. Unpleasant and bitter tasting antibiotics include gyrase inhibitors; particularly, those of the naphthyridone-carboxylic acid and quinolone-carboxylic acid types; more particularly, those selected from levofloxacin, ciprofloxacin, norfloxacin, ofloxacin or enoxacin.

In view of these difficulties, it would be desirable to develop a ready-to-use taste masked liquid pharmaceutical dosage form, in particular, a solution or suspension. More particularly, there exists a need for a taste masked suspension dosage form that minimizes sedimentation of the pharmaceutically active agent, provides uniform distribution of the active agent and has a palatable taste.

An object of the present invention is to provide a taste masked liquid pharmaceutical composition comprising a pharmaceutically active agent and a taste masking composition.

An object of the present invention is to provide a taste masked liquid pharmaceutical composition comprising a pharmaceutically active agent and a taste masking composition wherein the taste masking composition comprises a taste masking effective amount of an artificial sweetener.

An object of the present invention is to provide a taste masked liquid pharmaceutical composition wherein the pharmaceutically active agent is bitter tasting.

An object of the present invention is to provide a taste masked liquid pharmaceutical composition wherein the bitter tasting pharmaceutically active agent is an antibiotic.

An object of the present invention is to provide a taste masked liquid pharmaceutical composition wherein the bitter tasting antibiotic is levofloxacin.

An object of the present invention is to provide a taste masked liquid pharmaceutical composition wherein the taste masking effective amount of an artificial sweetener masks a bitter taste.

An object of the present invention is to provide a taste masked liquid pharmaceutical composition wherein the taste masking composition comprises a taste masking effective amount of sucralose.

An object of the present invention is to provide a taste masked liquid pharmaceutical composition wherein the taste masking composition further comprises a taste masking effective amount of an artificial sweetener and at least one flavoring agent.

An object of the present invention is to provide a taste masked liquid pharmaceutical composition wherein the taste masking composition further comprises a taste masking effective amount of an artificial sweetener, at least one flavoring agent, an optional sweetening agent and an optional debittering agent or mixtures thereof.

SUMMARY OF THE INVENTION

The present invention provides a taste masked liquid pharmaceutical composition comprising a pharmaceutically active agent and a taste masking composition.

The present invention provides a taste masked liquid pharmaceutical composition comprising a pharmaceutically active agent and a taste masking composition wherein the taste masking composition comprises a taste masking effective amount of an artificial sweetener.

An embodiment of the invention is a taste masked liquid pharmaceutical composition wherein the pharmaceutically active agent is bitter tasting.

An embodiment of the invention is a taste masked liquid pharmaceutical composition wherein the bitter tasting pharmaceutically active agent is an antibiotic.

An embodiment of the invention is a taste masked liquid pharmaceutical composition wherein the bitter tasting antibiotic is levofloxacin.

An embodiment of the invention is a taste masked liquid pharmaceutical composition wherein the taste masking effective amount of an artificial sweetener masks a bitter taste.

An embodiment of the invention is a taste masked liquid pharmaceutical composition wherein the taste masking composition comprises a taste masking effective amount of the artificial sweetener sucralose.

An embodiment of the invention is a taste masked liquid pharmaceutical composition wherein the taste masking composition further comprises a taste masking effective amount of an artificial sweetener and at least one flavoring agent.

An embodiment of the invention is a taste masked liquid pharmaceutical composition wherein the taste masking composition further comprises a taste masking effective amount of the artificial sweetener sucralose and at least one flavoring agent.

An embodiment of the invention is a taste masked liquid pharmaceutical composition wherein the taste masking composition further comprises a taste masking effective amount of an artificial sweetener, at least one flavoring agent, an optional sweetening agent and an optional debittering agent or mixtures thereof.

An embodiment of the invention is a taste masked liquid pharmaceutical composition wherein the taste masking composition further comprises a taste masking effective amount of the artificial sweetener sucralose, at least one flavoring agent, an optional sweetening agent and an optional debittering agent or mixtures thereof.

DETAILED DESCRIPTION OF THE INVENTION

The present invention provides a taste masked liquid pharmaceutical composition comprising a pharmaceutically active agent and a taste masking composition.

The present invention provides a taste masked liquid pharmaceutical composition comprising a pharmaceutically active agent and a taste masking composition wherein the taste masking composition comprises a taste masking effective amount of an artificial sweetener.

In an embodiment of the present invention, the pharmaceutically active agent is bitter tasting and includes, but is not limited to, those selected from antibiotics, analgesics, anti-inflammatory drugs, antihistamines, antibacterials, antimicrobials, decongestants, anti-depressants, antipsychotics, antivirals, oncolytics, vaccines, antiepileptics, anti-asthma compounds or antispasmodics.

In an embodiment of the present invention, the bitter tasting pharmaceutically active agent is an antibiotic and includes, but is not limited to, those selected from a naphthyridone-carboxylic acid type antibiotic, a quinolone-carboxylic acid type antibiotic, a cephalosporin type antibiotic, a macrolide type antibiotic or a penicillin type antibiotic and the like.

In a preferred embodiment of the present invention, the bitter tasting pharmaceutically active agent is a quinolone-carboxylic acid antibiotic and includes, but is not limited to, those selected from levofloxacin, ciprofloxacin, norfloxacin, ofloxacin or enoxacin.

In a more preferred embodiment of the present invention, the bitter tasting quinolone-carboxylic acid antibiotic is levofloxacin (marketed under the tradename LEVAQUIN®), a compound having the CAS (Chemical Abstracts Society) Registry Number: 100986-85-4 and the CAS Index Name: (3S)-9-fluoro-2,3-dihydro-3-methyl-10-(4-methyl-1-piperazinyl)-7-oxo-7H-pyrido[1,2,3-de]-1,4-benzoxazine-6-carboxylic acid.

The pharmaceutically active agent is present in the composition in a therapeutically effective amount, which amount produces the desired therapeutic response and can be readily determined by one skilled in the art. In determining such an amount, the particular compound being administered, the bioavailability characteristics of the pharmaceutically active agent, the dose regimen, the method of administration, the age and weight of the patient and other factors must be considered.

In an embodiment of the present invention, the bitter tasting pharmaceutically active agent is a therapeutically effective amount of levofloxacin; wherein the therapeutically effective amount has a range of from about 1 gram to about 5 grams of levofloxacin per 100 mL. In a further embodiment, the therapeutically effective amount has a range of from about 2.5 grams to about 5 grams of levofloxacin per 100 mL. In preferred embodiments of the present invention, the therapeutically effective amount is selected from about 1 gram of levofloxacin per 100 mL, about 2.5 grams of levofloxacin per 100 mL or about 5 grams of levofloxacin per 100 mL.

In an embodiment of the present invention, the liquid pharmaceutical composition is a solution, syrup or suspension for oral administration to adult and pediatric patients comprising a therapeutically effective amount of a bitter tasting pharmaceutically active agent and a taste masking composition.

In an embodiment of the present invention, the taste masking composition comprises a taste masking effective amount of an artificial sweetener.

In general, the total amount of the taste masking composition present in a taste masked liquid pharmaceutical composition comprises from about 70 to 90% weight to volume of the total liquid composition; preferably, about 80% weight to volume. The present invention is not limited to this amount but rather to a taste masking effective amount, whereby the taste of the bitter tasting pharmaceutically active agent is masked and the liquid pharmaceutical composition is palatable to the intended consumer, such as a pediatric or adult patient in need thereof.

For example, the use of a highly intense artificial sweetener would require a lower amount of a sweetening agent compared to the use of a sugar sweetener to achieve a taste masking effective amount. The taste masking effective amount required varies with the amount of the pharmaceutically active agent used and the intensity of the unpalatable taste.

In the present invention, we have surprisingly discovered that a taste masking effective amount of an artificial sweetener unexpectedly masks the taste of a bitter tasting pharmaceutically active agent.

Artificial sweeteners that may be used in the present invention include, and are not limited to, aspartame, acesulfame potassium, cyclamate, saccharin, saccharin sodium, sucralose or mixtures thereof. The taste masking effective amount of an artificial sweetener is that amount whereby the taste of the bitter tasting pharmaceutically active agent is masked and the liquid pharmaceutical composition is palatable.

Aspartame is used as a table-top sweetener and in beverage and food products and pharmaceutical and vitamin preparations to enhance flavor systems and to mask some unpleasant taste characteristics. Comparatively, aspartame has approximately 180–200 times the sweetening power of sucrose. The taste masking effective amount of aspartame has a range of from about 0.15 to about 8 grams per 100 mL.

Acesulfame potassium is used as a table-top sweetener and in cosmetics, beverage and food products and pharmaceutical and vitamin preparations to enhance flavor systems and to mask some unpleasant taste characteristics. Comparatively, acesulfame potassium has approximately 180–200 times the sweetening power of sucrose. The taste masking effective amount of acesulfame potassium has a range of from about 0.15 to about 8 grams per 100 mL.

Cyclamate is used as a table-top sweetener and in beverage and food products. Comparatively, cyclamate has approximately 30 times the sweetening power of sucrose. The taste masking effective amount of cyclamate has a range of from about 1 to about 50 grams per 100 mL.

Saccharin is used to enhance flavor systems and to mask some unpleasant taste characteristics and has approximately 500 times the sweetening power of sucrose. The taste masking effective amount of saccharin has a range of from about 0.08 to about 3 grams per 100 mL.

Saccharin sodium is considerably more soluble in water than saccharin, is used more frequently in pharmaceutical formulations and has approximately 300 times the sweetening power of sucrose. The taste masking effective amount of saccharin sodium has a range of from about 0.1 to about 5 grams per 100 mL.

Sucralose (marketed under the tradename SPLENDA®) is a compound having the CAS Registry Number: 56038-13-2 and the CAS Index Name: 1,6-dideoxy-b-D-fructofuranosyl-4-chloro-4-deoxy-α-D-galactopyranoside and is characterized as an intensely sweet, trichlorinated carbohydrate, structurally similar to sucrose, having approximately 600 times the sweetening power of sucrose.

Mixtures of artificial sweeteners, such as a ratio of 10 parts cyclamate to 1 part saccharin, have also been found to have synergistic sweetening properties and improve taste characteristics.

A preferred embodiment of the taste masking composition comprises a taste masking effective amount of the artificial sweetener sucralose. The amount of sucralose used causes sucralose to mask the taste of the bitter tasting pharmaceutically active agent. The present invention thereby intends that sucralose be used in a taste masking effective amount in a plurality of liquid pharmaceutical compositions wherein the pharmaceutically active agent is bitter tasting to make the liquid pharmaceutical compositions palatable.

Preferably, the taste masking effective amount of sucralose has a range of from about 0.05 to about 2.5 grams per 100 mL. More preferably, the taste masking effective amount of sucralose has a range of from about 0.45 to about 1.7 grams per 100 mL. More preferably, the taste masking effective amount of sucralose is about 1 gram per 100 mL.

Another embodiment of the taste masking composition further comprises a taste masking effective amount of an artificial sweetener and at least one flavoring agent.

The flavoring agent used is of the type and amount desired to enhance the palatability of the particular liquid pharmaceutical composition to the intended consumer. Flavoring agents that may be used in the present invention include, and are not limited to, natural flavors, natural fruit flavors, artificial flavors, artificial fruit flavors, flavor enhancers or mixtures thereof. Natural flavors, artificial flavors or mixtures thereof include, and are not limited to, mint (such as peppermint or spearmint), menthol, cinnamon, vanilla, artificial vanilla, chocolate, artificial chocolate or bubblegum. Natural fruit flavors, artificial fruit flavors or mixtures thereof include, and are not limited to, cherry, grape, orange, strawberry or lemon. Flavor enhancers include, and are not limited to, citric acid. Although flavoring agents are generally provided as a minor component of the taste masking composition in amounts effective to provide a palatable flavor to the liquid pharmaceutical composition, the addition of at least one flavoring agent is preferred; and, more preferably, up to two flavoring agents may be employed. A flavoring agent used in the taste masking composition has a range of from about 0.02 to about 0.06 grams per 100 mL. Preferably, a flavoring agent is present in a range of from about 0.03 to about 0.04 grams per 100 mL.

Another embodiment of the taste masking composition further comprises a taste masking effective amount of an artificial sweetener, at least one flavoring agent, an optional sweetening agent and an optional debittering agent or mixtures thereof.

Optional sweetening agents include, but are not limited to, sugar sweeteners such as monosaccharides, disaccharides and polysaccharides. Examples of suitable sugar sweeteners include but are not limited to xylose, ribose, glucose, mannose, galactose, fructose, dextrose, sucrose, maltose, partially hydrolyzed starch (such as maltitol syrup) or corn syrup solids and sugar alcohols such as sorbitol, xylitol, mannitol, glycerin and combination thereof. Preferably, the type of glycerin used is U.S.P. grade. Preferred as a sugar sweetener is high fructose corn syrup. The amount of sugar sweetener used in the taste masking composition will vary depending on the degree of palatability desired for the liquid pharmaceutical composition. Generally the total amount of sugar sweetener used has a range of from 0 to about 120 grams per 100 mL. Preferably, the amount of sugar sweetener used has a range of from about 50 grams to about 110 grams per 100 mL.

Optional sweetening agents include artificial sweeteners used in addition to sugar sweeteners. Preferably, other artificial sweeteners include, and are not limited to, aspartame, acesulfame potassium, cyclamate, saccharin, saccharin sodium, sucralose or mixtures thereof. The optional amount of artificial sweeteners used in the taste masking composition will vary depending on the degree of palatability desired for the liquid pharmaceutical composition. Generally, the amount of an optional artificial sweetener used in the taste masking composition has a range of from about 0 to about 1.5 grams per 100 mL.

In general, one optional debittering agent is employed in a taste masking composition of the present invention. Optional debittering agents include, and are not limited to, natural debittering agents, artificial debittering agents or debittering agents which inhibit a chemosensory response in the mouth or nose or mixtures thereof. Debittering agents for use in the present invention are commercially available, such as those marketed under the names Prosweet FL N&A K (by Virginia Dare), Bitterness Modifier 36734 (by Bush, Boake and Allen, Inc.), Natural Taste Masker 501.441/A and Special Taste Masker Compound 501.437/A (by Firmenich, Inc.), and may be identified by those skilled in the art.

Accordingly, a natural debittering agent, artificial debittering agent or chemosensory response inhibitor agent present in the taste masking composition has a range of from about 0 grams to about 1 gram per 100 mL. Preferably, a debittering agent has a range of from about 0.01 to about 0.2 grams per 100 mL. More preferably, a debittering agent has a range of from about 0.03 to about 0.05 grams per 100 mL.

An embodiment of the invention is a taste masked liquid pharmaceutical composition wherein the pharmaceutical composition is a suspension comprising a pharmaceutically active agent and a taste masking composition.

An embodiment of the invention is a taste masked liquid pharmaceutical composition wherein the pharmaceutical composition is a suspension comprising a pharmaceutically active agent and a taste masking composition wherein the taste masking composition comprises a taste masking effective amount of an artificial sweetener.

An embodiment of the invention is a taste masked liquid pharmaceutical composition wherein the pharmaceutical composition is a suspension comprising a bitter tasting pharmaceutically active agent and a taste masking composition.

An embodiment of the invention is a taste masked liquid pharmaceutical composition wherein the pharmaceutical composition is a suspension comprising a bitter tasting antibiotic and a taste masking composition.

An embodiment of the invention is a taste masked liquid pharmaceutical composition wherein the pharmaceutical composition is a suspension comprising the bitter tasting antibiotic levofloxacin and a taste masking composition.

An embodiment of the invention is a taste masked liquid pharmaceutical suspension wherein the taste masking effective amount of an artificial sweetener masks a bitter taste.

An embodiment of the invention is a taste masked liquid pharmaceutical suspension wherein the taste masking composition comprises a taste masking effective amount of the artificial sweetener sucralose.

An embodiment of the invention is a taste masked liquid pharmaceutical suspension wherein the taste masking composition further comprises a taste masking effective amount of an artificial sweetener and at least one flavoring agent.

An embodiment of the invention is a taste masked liquid pharmaceutical suspension wherein the taste masking composition further comprises a taste masking effective amount of the artificial sweetener sucralose and at least one flavoring agent.

An embodiment of the invention is a taste masked liquid pharmaceutical suspension wherein the taste masking composition further comprises a taste masking effective amount of an artificial sweetener, at least one flavoring agent, an optional sweetening agent and an optional debittering agent or mixtures thereof.

An embodiment of the invention is a taste masked liquid pharmaceutical suspension wherein the taste masking composition further comprises a taste masking effective amount of the artificial sweetener sucralose, at least one flavoring agent, an optional sweetening agent and an optional debittering agent or mixtures thereof.

An embodiment of the invention is a taste masked liquid pharmaceutical suspension wherein the suspension comprises a polysaccharide gum and a microcrystalline cellulose or a carboxymethylcellulose or a mixture thereof.

An embodiment of the invention is a taste masked liquid pharmaceutical suspension wherein the suspension comprises a polysaccharide gum selected from a high molecular weight polysaccharide gum and a microcrystalline cellulose or a carboxymethylcellulose selected from carboxymethylcellulose or a metal salt thereof, wherein the metal salt is selected from calcium, sodium or potassium.

An embodiment of the invention is a taste masked liquid pharmaceutical suspension wherein the suspension comprises a high molecular weight polysaccharide gum selected from xanthan, tragacanth, guar or carageenan and a microcrystalline cellulose or a carboxymethylcellulose selected from carboxymethylcellulose or a metal salt thereof, wherein the metal salt is selected from calcium, sodium or potassium.

An embodiment of the invention is a taste masked liquid pharmaceutical suspension wherein the suspension comprises a xanthan gum and a mixture of microcrystalline cellulose and sodium carboxymethylcellulose.

The preferred polysaccharide gum for use in a taste masked liquid pharmaceutical suspension is xanthan gum, a high molecular weight polysaccharide gum produced by *Xanthomonas campestris*. Techniques and strains for producing this polysaccharide are described in U.S. Pat. Nos. 4,752,580 and 3,485,719 (the disclosures of which are hereby incorporated by reference). Preferably, the gum used in the present invention should have a viscosity in a 1% salt solution of from about 1000 to about 1700 cP (mPa-sec), as measured at 25° C. with an LV model Brookfield Synchro-Lectric viscometer at 60 rpm, no. 3 spindle.

Preferably, the amount of xanthan gum present has a range of from about 0.05 to about 0.25 gram per 100 mL. More preferably, xanthan gum has a range of from about 0.09 to about 0.20 gram per 100 mL. Most preferably, the amount of xanthan gum present is about 0.14 gram per 100 mL.

A preferred embodiment of the invention is a taste masked liquid pharmaceutical suspension wherein the suspension comprises a polysaccharide gum and a mixture of microcrystalline cellulose and a carboxymethylcellulose.

The preferred mixture of microcrystalline cellulose and a carboxymethylcellulose comprises a commercially available dried coprecipitated microcrystal of cellulose in a mixture with sodium carboxymethylcellulose. Sodium carboxymethylcellulose is commonly used as the coprecipitate in microcrystalline cellulose. It is preferable that sodium carboxymethylcellulose be present in the range of from about 8 weight percent to about 19 weight percent of the total weight of the mixture of microcrystalline cellulose and sodium carboxymethylcellulose. Preferred microcrystalline cellulose and sodium carboxymethylcellulose mixtures have sodium carboxymethylcellulose present in the range of from about 8 to about 14 weight percent. These mixtures are commercially available from FMC under the trademark Avicel® CL-611, Avicel® RC-581 and Avicel® RC-591. Avicel® RC-591 is the preferred mixture of microcrystalline cellulose and sodium carboxymethylcellulose for use in the suspension and contains about 8.3 to about 13.8 weight percent sodium carboxymethylcellulose, with the remainder being microcrystalline cellulose.

Preferably, the mixture of microcrystalline cellulose and sodium carboxymethylcellulose is present in a range of from about 0.4 to about 1.0 gram per 100 mL. Preferably, the mixture has a range of from about 0.6 to about 0.8 gram per 100 mL. More preferably, about 0.7 gram per 100 mL of the mixture is present.

A preferred embodiment of the suspension comprises a weight ratio of xanthan gum to the mixture of microcrystalline cellulose and sodium carboxymethylcellulose wherein the weight ratio is maintained in a range of between about 1:4 to 1:8. Preferably, the weight ratio is maintained in a range of about 1:6.

A preferred embodiment of the suspension comprises limiting the amount of water present to that amount necessary to hydrate the xanthan gum and the mixture of microcrystalline cellulose and sodium carboxymethylcellulose while providing a sufficient aqueous base to impart the desired degree of viscosity.

The total amount of water present in the suspension has a range of from about 5 to about 60 grams per 100 mL. Preferably, water has a range of from about 10 to about 30 grams per 100 mL. More preferably, water has a range of from about 10 to about 20 grams per 100 mL. Most preferably, about 15 grams of water is present per 100 mL of suspension.

An embodiment of the invention is a taste masked liquid pharmaceutical composition wherein the pharmaceutical composition is a solution comprising a pharmaceutically active agent and a taste masking composition.

An embodiment of the invention is a taste masked liquid pharmaceutical composition wherein the pharmaceutical composition is a solution comprising a pharmaceutically active agent and a taste masking composition wherein the taste masking composition comprises a taste masking effective amount of an artificial sweetener.

An embodiment of the invention is a taste masked liquid pharmaceutical composition wherein the pharmaceutical composition is a solution comprising a bitter tasting pharmaceutically active agent and a taste masking composition.

An embodiment of the invention is a taste masked liquid pharmaceutical composition wherein the pharmaceutical composition is a solution comprising a bitter tasting antibiotic and a taste masking composition.

An embodiment of the invention is a taste masked liquid pharmaceutical composition wherein the pharmaceutical composition is a solution comprising the bitter tasting antibiotic levofloxacin and a taste masking composition.

An embodiment of the invention is a taste masked liquid pharmaceutical solution wherein the taste masking effective amount of an artificial sweetener masks a bitter taste.

An embodiment of the invention is a taste masked liquid pharmaceutical solution wherein the taste masking composition comprises a taste masking effective amount of the artificial sweetener sucralose.

An embodiment of the invention is a taste masked liquid pharmaceutical solution wherein the taste masking composition further comprises a taste masking effective amount of an artificial sweetener and at least one flavoring agent.

An embodiment of the invention is a taste masked liquid pharmaceutical solution wherein the taste masking composition further comprises a taste masking effective amount of the artificial sweetener sucralose and at least one flavoring agent.

An embodiment of the invention is a taste masked liquid pharmaceutical solution wherein the taste masking composition further comprises a taste masking effective amount of an artificial sweetener, at least one flavoring agent, an optional sweetening agent and an optional debittering agent or mixtures thereof.

An embodiment of the invention is a taste masked liquid pharmaceutical solution wherein the taste masking composition further comprises a taste masking effective amount of the artificial sweetener sucralose, at least one flavoring agent, an optional sweetening agent and an optional debittering agent or mixtures thereof.

The taste masked liquid pharmaceutical composition of the present invention may optionally contain pH stabilizers (such as, but not limited to, citric acid, ascorbic acid, potassium phosphate or sodium phosphate), pH buffers (such as, but not limited to, citric acid, ascorbic acid, potassium phosphate or sodium phosphate), wetting agents (such as, but not limited to, sodium laurel sulfate or docusate sodium), preservatives, coloring agents (such as, but not limited to, dyes, lake dyes or natural coloring), defoaming agents (such as, but not limited to, simethicone), surfactants (such as, but not limited to, sorbitan oleate ester or polyoxyethylene sorbitan monooleate), electrolytes (such as, but not limited to, sodium chloride, potassium chloride or sodium bicarbonate) or sequestering agents (such as, but not limited to, EDTA (ethylene diamine tetraacetic acid and the salts thereof)).

A pH stabilizer such as citric acid may be optionally added to the taste masked liquid pharmaceutical composition of the present invention to stabilize pH and prevent microbial growth. Citric acid is advantageously added since a lower pH will prevent microbial growth and add to the stability of the product.

A pH buffer may be optionally added to the taste masked liquid pharmaceutical composition of the present invention to maintain pH in a desired range or to enhance the solubility of the pharmaceutically active agent. Suitable buffers are those that are not chemically reactive with other ingredients and are present in amounts sufficient to provide the desired degree of pH buffering.

When the taste masked liquid pharmaceutical composition is a suspension, the solubility of the pharmaceutically active agent is reduced by maintaining pH in a range of from about pH 6 to about pH 8; preferably, about pH 7. Preferably, a buffer is optionally present in a suspension in a range of up to about 1 gram per 100 mL. More preferably, a buffer is not present in a suspension since the pharmaceutically active agent (in particular, levofloxacin) acts as an autobuffering agent to stabilize pH at about pH 7.

When the taste masked liquid pharmaceutical composition is a solution, the solubility of the pharmaceutically active agent is increased by maintaining pH in a range of from about pH 3 to about pH 6; preferably, about pH 5. Preferably, a buffer is present in a solution in a range of from 0.01 to 1 gram per 100 mL.

Wetting agents may be employed in the taste masked liquid pharmaceutical composition to facilitate the dispersion of hydrophobic pharmaceutically active agents. Preferably, a minimal concentration of wetting agents should be selected to achieve optimum dispersion of the pharmaceutically active agent. It should be appreciated that an excess concentration of wetting agent may cause flocculation. Those skilled in the art are well versed in suitable empirical methods to determine the appropriate wetting agents and concentrations to achieve optimum dispersion and avoid flocculation. Suitable wetting agents are listed in the U.S. Pharmacoepia XXI.

Preservatives useful in the present invention include but are not limited to sodium benzoate, potassium sorbate, salts of edetate (also known as salts of ethylenediaminetetraacetic acid, or EDTA, such as disodium edetate), parabens (such as methyl, ethyl, propyl and butyl p-hydroxybenzoic acids esters or mixtures thereof) or mixtures thereof. The preservatives listed above are exemplary, but each preservative must be evaluated on an empirical basis, in each composition, to assure the compatibility and efficacy of the preservative. Methods for evaluating the efficacy of preservatives in liquid pharmaceutical compositions are known to those skilled in the art. Sodium benzoate, propylparaben, butylparaben or mixtures thereof are preferred preservative ingredients and may be added to a taste masked liquid pharmaceutical composition although other pharmaceutically acceptable preservatives may be substituted therefor.

Preservatives may be present in amounts of up to about 1 gram per 100 mL. Preferably, an individual preservative may be present in an amount in the range of from about 0.015 to about 0.5 gram per 100 mL. Preferably, a preservative such as propylparaben, butylparaben or mixtures thereof is present in a range of from about 0.01 to about 0.05 gram per 100 mL. More preferably, about 0.006 gram per 100 mL of a preservative selected from propylparaben, butylparaben or mixtures thereof is present.

A preservative such as sodium benzoate may be optionally present in a range of from about 0.1 to about 0.5 gram per 100 mL. More preferably, about 0.2 gram per 100 mL sodium benzoate is present.

Coloring agents also may be incorporated to provide an appealing color to the taste masked liquid pharmaceutical composition. Suitable coloring agents are well known to those skilled in the art and are those that avoid chemical incompatibilities with other ingredients.

In order to further illustrate the present invention and the advantages thereof, the following specific examples are given with the understanding that these examples are intended only to be illustrations without serving as a limitation on the scope of the present invention.

Several embodiments of the present liquid pharmaceutical composition comprising an antibiotic and a taste masking composition are herein provided wherein the solution or suspension has superior taste masking characteristics and is stable and pourable.

EXAMPLE 1

Manufacturing Procedure for a Taste Masked Liquid Pharmaceutical Suspension

Using the appropriate equipment and conditions for the desired batch size, a taste masked pharmaceutical suspension is prepared as follows:

1. Add the liquid ingredients (except glycerin) and an appropriate amount of purified water in a first container;
2. Mix the liquids with an appropriate mixer;
3. Add the dry ingredients (except xanthan gum) and the pharmaceutically active agent to the mixed liquid portion;
4. Mix the liquid portion and dry ingredients with an appropriate mixer;
5. Prepare a xanthan gum-glycerin slurry by placing the glycerin in a second container, adding xanthan gum and dispersing the xanthan gum with an appropriate mixer;
6. Transfer the xanthan gum-glycerin slurry to the first container and mix with an appropriate mixer for an appropriate amount of time;
7. Add the flavoring and coloring agents to the first container and mix with an appropriate mixer;
8. Add purified water as needed to bring the batch to the final batch weight; and,
9. Mix the ingredients, slurry and agents for an appropriate amount of time, thereby forming the suspension.

EXAMPLE 2a

Manufacturing Procedure for a Taste Masked Liquid Pharmaceutical Solution

Using the appropriate equipment and conditions for the desired batch size, a taste masked pharmaceutical solution is prepared as follows:

1. Add a sorbitol solution and an appropriate amount of purified water in a first container;
2. Mix the sorbitol solution and water with an appropriate mixer;
3. Prepare a paraben-glycerin slurry by placing the glycerin in a second container, adding butylparaben and propylparaben and dispersing the parabens with an appropriate mixer;
4. Transfer the paraben-glycerin slurry to the first container and mix with an appropriate mixer for an appropriate amount of time;
5. Add the remaining liquid ingredients to the first container and mix with an appropriate mixer for an appropriate amount of time;
6. Add the dry ingredients and the pharmaceutically active agent to the first container and mix with an appropriate mixer for an appropriate amount of time;
7. Add the flavoring and coloring agents to the first container and mix with an appropriate mixer;
8. Adjust pH to a desired value as needed by adding an appropriate acid or base;
9. Add purified water as needed to bring the batch to the final batch weight; and,
10. Mix the ingredients, slurry and agents for an appropriate amount of time, thereby forming the solution.

EXAMPLE 2b

Manufacturing Procedure for a Taste Masked Liquid Pharmaceutical Solution

Using the appropriate equipment and conditions for the desired batch size, an alternative method for preparing a taste masked pharmaceutical solution is as follows:

1. Add an appropriate amount of purified water in a first container;
2. Add sucrose and sucralose to the first container and mix with an appropriate mixer for an appropriate amount of time;
3. Prepare a paraben-glycerin slurry by placing the glycerin in a second container, adding butylparaben and propylparaben and dispersing the parabens with an appropriate mixer;
4. Transfer the paraben-glycerin slurry to the first container and mix with an appropriate mixer for an appropriate amount of time;
5. Add an appropriate amount of purified water to a third container and adjust pH to a desired acidic value as needed by adding an appropriate acid to the third container;
6. Transfer the acidified water to the first container and mix with an appropriate mixer for an appropriate amount of time;
7. Add the pharmaceutically active agent to the first container and mix with an appropriate mixer for an appropriate amount of time;
8. Add the flavoring and coloring agents to the first container and mix with an appropriate mixer;
9. Add purified water as needed to bring the batch to the final batch weight; and,
10. Mix the ingredients, slurry and agents for an appropriate amount of time, thereby forming the solution.

EXAMPLE 3

Taste Masked Suspension Ingredient Ranges

The ranges for the components used in preferred embodiments of the taste masked pharmaceutical composition of the present invention, wherein the composition comprises a suspension are indicated as follows:

| Quantitative Composition of a Suspension (250 mg/5 mL) | |
| --- | --- |
| Component | Range % W/V |
| Levofloxacin Hemihydrate | 1–5.2 |
| Glycerin, USP | 2.5–20 |
| Sucrose, Extra Fine Granular NF | 10–60 |
| High Fructose Corn Syrup 55% | 20–75 |
| Sorbitol Solution, USP | 10–70 |
| Purified Water | 5–25 |
| Microcrystalline Cellulose and Sodium Carboxymethyl Cellulose, NF | 0.1–1.4 |
| Sodium Benzoate, NF | 0.01–0.5 |
| Propylparaben, NF | 0.01–0.03 |
| Butylparaben, NF | 0.006–0.05 |

-continued

| Quantitative Composition of a Suspension (250 mg/5 mL) | |
|---|---|
| Component | Range % W/V |
| Citric Acid, Anhydrous USP | 0.005–1.0 |
| Sucralose NF (pure substance, not marketed) | 0.05–2.5 |
| Xanthan Gum USP, EP, JPE | 0.05–0.25 |
| Flavoring Agent(s) | 0.02–0.06 |
| Debittering Agent(s) | 0.0–1.0 |
| Sweetening Agent(s) | 0.0–121.5 |
| Purified Water (bring to 100% w/v) | as needed |

EXAMPLES 4–11

Taste Masked Suspensions

Embodiments of the present invention are herein described, wherein a taste masked liquid pharmaceutical suspension comprises levofloxacin and a taste masking effective amount of an artificial sweetener.

EXAMPLE 4

| Quantitative Composition of a Levofloxacin Liquid Suspension (250 mg/5 mL) | |
|---|---|
| Component | % W/V |
| Levofloxacin Hemihydrate | 5.123 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Sodium Benzoate, NF | 0.2 |
| Propylparaben, NF | 0.015 |
| Citric Acid, Anhydrous USP | 0.075 |
| Sucralose NF (pure substance, not marketed) | 1.02 |
| Xanthan Gum USP, EP, JPE | 0.12 |
| Peppermint Flavor | 0.03 |
| Purified Water (qs to 100% w/v) | as needed |

EXAMPLE 5

| Quantitative Composition of a Levofloxacin Liquid Suspension (125 mg/5 mL) | |
|---|---|
| Component | % W/V |
| Levofloxacin Hemihydrate | 2.5615 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Butylparaben, NF | 0.020 |
| Propylparaben, NF | 0.030 |
| Citric Acid, Anhydrous USP | 0.075 |
| Sucralose NF (pure substance, not marketed) | 1.02 |
| Xanthan Gum USP, EP, JPE | 0.12 |
| Lemon Flavor | 0.05 |

-continued

| Quantitative Composition of a Levofloxacin Liquid Suspension (125 mg/5 mL) | |
|---|---|
| Component | % W/V |
| Peppermint Flavor | 0.04 |
| Purified Water (qs to 100% w/v) | as needed |

EXAMPLE 6

| Quantitative Composition of a Levofloxacin Liquid Suspension (250 mg/5 mL) | |
|---|---|
| Component | % W/V |
| Levofloxacin Hemihydrate | 5.123 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Butylparaben, NF | 0.02 |
| Propylparaben, NF | 0.03 |
| Citric Acid, Anhydrous USP | 0.075 |
| Sucralose NF (pure substance, not marketed powder) | 1.02 |
| Xanthan Gum USP, EP, JPE | 0.12 |
| Artificial Vanilla Mint Flavor | 0.04 |
| Natural Taste Masker Compound | 0.04 |
| Purified Water (qs to 100% w/v) | as needed |

EXAMPLE 7

| Quantitative Composition of a Levofloxacin Liquid Suspension (250 mg/5 mL) | |
|---|---|
| Component | % W/V |
| Levofloxacin Hemihydrate | 5.123 |
| Glycerin, USP | 10 |
| Sucrose, Extra Fine Granular NF | 20 |
| High Fructose Corn Syrup 55% | 50 |
| Sorbitol Solution, USP | 20 |
| Microcrystalline Cellulose and Sodium Carboxymethyl Cellulose, NF | 0.7 |
| Butylparaben, NF | 0.02 |
| Propylparaben, NF | 0.03 |
| Citric Acid, Anhydrous USP | 0.075 |
| Sucralose NF (pure substance, not marketed powder) | 1.02 |
| Xanthan Gum USP, EP, JPE | 0.12 |
| Peppermint Flavor | 0.3 |
| Purified Water (qs to 100% w/v) | as needed |

EXAMPLE 8

| Quantitative Composition of a Levofloxacin Liquid Suspension (250 mg/5 mL) | |
|---|---|
| Component | % W/V |
| Levofloxacin Hemihydrate | 5.123 |
| Glycerin, USP | 10 |

-continued

Quantitative Composition of a Levofloxacin Liquid Suspension
(250 mg/5 mL)

| Component | % W/V |
|---|---|
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Butylparaben, NF | 0.02 |
| Propylparaben, NF | 0.03 |
| Citric Acid, Anhydrous USP | 0.075 |
| Sucralose NF (pure substance, not marketed powder) | 1.02 |
| Xanthan Gum USP, EP, JPE | 0.12 |
| Artificial Chocolate Flavor | 0.05 |
| Peppermint Flavor | 0.03 |
| Natural Taste Masker Compound | 0.04 |
| Purified Water (qs to 100% w/v) | as needed |

EXAMPLE 9

Quantitative Composition of a Levofloxacin Liquid Suspension
(250 mg/5 mL)

| Component | % W/V |
|---|---|
| Levofloxacin Hemihydrate | 5.123 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Butylparaben, NF | 0.02 |
| Propylparaben, NF | 0.03 |
| Citric Acid, Anhydrous USP | 0.075 |
| Sucralose NF (pure substance, not marketed powder) | 1.02 |
| Xanthan Gum USP, EP, JPE | 0.12 |
| Artificial Cherry Flavor | 0.04 |
| Peppermint Flavor | 0.03 |
| Artificial Taste Masker Compound | 0.04 |
| Purified Water (qs to 100% w/v) | as needed |

EXAMPLE 10

Quantitative Composition of a Levofloxacin Liquid Suspension
(250 mg/5 mL)

| Component | % W/V |
|---|---|
| Levofloxacin Hemihydrate | 5.123 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Butylparaben, NF | 0.02 |
| Propylparaben, NF | 0.03 |
| Citric Acid, Anhydrous USP | 0.075 |
| Sucralose NF (pure substance, not marketed powder) | 1.02 |
| Xanthan Gum USP, EP, JPE | 0.12 |

-continued

Quantitative Composition of a Levofloxacin Liquid Suspension
(250 mg/5 mL)

| Component | % W/V |
|---|---|
| Artificial Bubblegum Flavor | 0.045 |
| Peppermint Flavor | 0.04 |
| Natural Taste Masker Compound | 0.04 |
| Purified Water (qs to 100% w/v) | as needed |

EXAMPLE 11

Quantitative Composition of a Levofloxacin Liquid Suspension
(250 mg/5 mL)

| Component | % W/V |
|---|---|
| Levofloxacin Hemihydrate | 5.123 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 15 |
| Microcrystalline Cellulose and Sodium Carboxymethyl Cellulose, NF | 0.7 |
| Butylparaben, NF | 0.02 |
| Propylparaben, NF | 0.03 |
| Citric Acid, Anhydrous USP | 0.075 |
| Sucralose NF (pure substance, not marketed powder) | 1.02 |
| Xanthan Gum USP, EP, JPE | 0.12 |
| Natural & Artificial Lemon Flavor | 0.04 |
| Peppermint Flavor | 0.045 |
| Natural Taste Masker Compound | 0.04 |
| Purified Water (qs to 100% w/v) | as needed |

EXAMPLE 12

Taste Masked Solution Ingredient Ranges

The ranges for the components used in preferred embodiments of the taste masked pharmaceutical composition of the present invention, wherein the composition comprises a solution are indicated as follows:

Quantitative Composition of a Solution
(250 mg/5 mL)

| Component | % W/V |
|---|---|
| Levofloxacin Hemihydrate | 2.5615 |
| Hydrochloric Acid (0.1 mL HCl 6N) | as needed |
| Sucrose, Extra Fine Granular NF | 20–50 |
| Sucralose NF (pure substance, not marketed) | 0.05–1.5 |
| Maltitol Solution (a blend of Hydrogenated Starch Hydrolysate 75% w/w solids) NF | 10–60 |
| Sorbitol Solution, USP | 10–70 |
| Glycerin, USP | 2.5–20 |
| Purified Water | 5–25 |
| Methylparaben, NF | 0.08–0.3 |
| Propylparaben, NF | 0.01–0.03 |
| Butylparaben, NF | 0.006–0.05 |
| Peppermint Flavor | 0.04–0.08 |
| Bubblegum Flavor | 0.04–0.06 |
| Special Taste Masker Compound | 0.04–0.06 |
| Purified Water (qs to 100% w/v) | as needed |

EXAMPLES 13–17

Taste Masked Solutions

Embodiments of the present invention are herein described, wherein a taste masked liquid pharmaceutical solution comprises levofloxacin and a taste masking effective amount of an artificial sweetener.

EXAMPLE 13

Quantitative Composition of a Levofloxacin Liquid Solution (125 mg/5 mL)

| Component | % W/V |
|---|---|
| Levofloxacin Hemihydrate | 2.5615 |
| Glycerin, USP | 10 |
| Sucrose, Extra Fine Granular NF | 20 |
| Maltitol Solution (a blend of Hydrogenated Starch Hydrolysate 75% w/w solids) NF | 50 |
| Sorbitol Solution, USP | 20 |
| Purified Water | 17 |
| Butylparaben, NF | 0.02 |
| Propylparaben, NF | 0.03 |
| Sucralose NF (pure substance, not marketed) | 1.02 |
| Peppermint Flavor | 0.04 |
| Bubblegum Flavor | 0.04 |
| Special Taste Masker Compound | 0.04 |
| Purified Water (qs to 100% w/v) | 100 |

EXAMPLE 14

Quantitative Composition of a Levofloxacin Liquid Solution (125 mg/5 mL)

| Component | % W/V |
|---|---|
| Levofloxacin Hemihydrate | 2.5615 |
| Glycerin, USP | 10 |
| Sucrose, Extra Fine Granular NF | 20 |
| High Fructose Corn Syrup 55% | 50 |
| Sorbitol Solution, USP | 20 |
| Purified Water | 17 |
| Butylparaben, NF | 0.02 |
| Propylparaben, NF | 0.03 |
| Sucralose NF (pure substance, not marketed) | 1.02 |
| Purified Water (qs to 100% w/v) | 100 |

EXAMPLE 15

Quantitative Composition of a Levofloxacin Liquid Solution (125 mg/5 mL)

| Component | % W/V |
|---|---|
| Levofloxacin Hemihydrate | 2.5615 |
| Hydrochloric Acid (0.1 mL HCl 6N) | as needed |
| Sucrose | 50 |
| Sucralose NF (pure substance, not marketed) | 0.5 |
| Glycerin, USP | 10 |
| Methylparaben, NF | 0.18 |
| Propylparaben, NF | 0.02 |
| Peppermint Flavor | 0.04 |
| Bubblegum Flavor | 0.04 |
| Special Taste Masker Compound | 0.05 |
| Purified Water (qs to 100% w/v) | as needed |

EXAMPLE 16

Quantitative Composition of a Levofloxacin Liquid Solution (125 mg/5 mL)

| Component | % W/V |
|---|---|
| Levofloxacin Hemihydrate | 2.5615 |
| Hydrochloric Acid (0.1 mL HCl 6N) | as needed |
| Sucrose | 50 |
| Sucralose NF (pure substance, not marketed) | 0.8 |
| Glycerin, USP | 10 |
| Methylparaben, NF | 0.18 |
| Propylparaben, NF | 0.02 |
| Peppermint Flavor | 0.05 |
| Bubblegum Flavor | 0.06 |
| Special Taste Masker Compound | 0.05 |
| Purified Water (qs to 100% w/v) | as needed |

EXAMPLE 17

Quantitative Composition of a Levofloxacin Liquid Solution (125 mg/5 mL)

| Component | % W/V |
|---|---|
| Levofloxacin Hemihydrate | 2.5615 |
| Hydrochloric Acid (0.1 mL HCl 6N) | as needed |
| Sucrose | 50 |
| Sucralose NF (pure substance, not marketed) | 0.8 |
| Glycerin, USP | 10 |
| Methylparaben, NF | 0.18 |
| Propylparaben, NF | 0.02 |
| Peppermint Flavor | 0.08 |
| Bubblegum Flavor | 0.06 |
| Special Taste Masker Compound | 0.05 |
| Purified Water (qs to 100% w/v) | as needed |

What is claimed is:

1. A taste-masked oral pharmaceutical solution comprising a quinolone-carboxylic acid antibiotic and a taste masking composition, said taste masking composition comprising from about 0.05 to about 2.5 grams of sucralose per 100 ml of the solution, up to about 120 grams of a sugar sweetener per 100 ml of the solution, and at least one flavoring agent.

2. The solution of claim 1, wherein the flavoring agent is selected from the group consisting of natural flavors, natural fruit flavors, artificial flavors, artificial fruit flavors, flavor enhancers and mixtures thereof.

3. The solution of claim 1 comprising at least two flavoring agents.

4. The solution of claim 1, wherein the sugar sweetener is sucrose.

5. The solution of claim 4, wherein the sugar sweetener further comprises glycerin.

6. The solution of claim 1, wherein the sugar sweetener is present in an amount of from about 50 grams to about 110 grams per 100 ml of the solution.

7. The solution of claim 1 further comprising a debittering agent.

8. The solution of claim 1, wherein the quinolone-carboxylic acid antibiotic is levofloxacin.

* * * * *